United States Patent
Sczakiel et al.

(10) Patent No.: US 11,008,574 B2
(45) Date of Patent: May 18, 2021

(54) ANTISENSE DRUGS AGAINST CANINE ICAM-1 FOR USE IN THE TREATMENT OF INFLAMMATION OF THE BUCCAL CAVITY

(71) Applicant: UNIVERSITÄT ZU LÜBECK, Lübeck (DE)

(72) Inventors: Georg Sczakiel, Groß Grönau (DE); Rosel Kretschmer-Kazemi Far, Lübeck (DE); Franziska Preuss, Lübeck (DE)

(73) Assignee: Universität zu Lübeck, Lübeck (DE)

( * ) Notice: Subject to any disclaimer, the term of this patent is extended or adjusted under 35 U.S.C. 154(b) by 0 days.

(21) Appl. No.: 16/634,019

(22) PCT Filed: Jul. 11, 2018

(86) PCT No.: PCT/EP2018/068750
§ 371 (c)(1),
(2) Date: Jan. 24, 2020

(87) PCT Pub. No.: WO2019/020371
PCT Pub. Date: Jan. 31, 2019

(65) Prior Publication Data
US 2020/0239894 A1    Jul. 30, 2020

(30) Foreign Application Priority Data
Jul. 28, 2017   (EP) .................... 17001305

(51) Int. Cl.
*C12N 15/113* (2010.01)
*A61K 9/00* (2006.01)

(52) U.S. Cl.
CPC ........ *C12N 15/1138* (2013.01); *A61K 9/0053* (2013.01)

(58) Field of Classification Search
CPC ............ C12N 15/1138; C12N 2310/11; A61K 9/0053; A61K 31/7088; A61P 1/02
See application file for complete search history.

(56) References Cited

U.S. PATENT DOCUMENTS

2004/0049022 A1    3/2004  Nyce et al.

FOREIGN PATENT DOCUMENTS

| WO | 2000018907 A2 | 4/2000 |
| WO | 2000018907 A3 | 4/2000 |
| WO | 2002085309 A2 | 10/2002 |
| WO | 2002085309 A9 | 10/2002 |
| WO | 2004011613 A2 | 2/2004 |
| WO | 2004011613 A3 | 9/2004 |

OTHER PUBLICATIONS

Kretschmer-Kazemi Far, R, et al., "Technical Improvements in the Computational Target Search for Antisense Oligonucleotides", Oligonucleotides 15, 223-233 (2005).
Nedbal, W, et al., "Advantages of Antisense Drugs for the Treatment of Oral Diseases", Antisense and Nucleic Acid Drug Development 12, 183-191 (2002).
Nedbal, W, et al., "Antisense-Mediated Inhibition of ICAM-1 Expression: A Therapeutic Strategy Against Inflammation of Human Periodontal Tissue", Antisense & Nucleic Acid Drug Development 12, 71-78 (2002).
Patent Cooperation Treaty, International Searching Authority, Search Report and Written Opinion for PCT/EP2018/068750, 18 pages, dated Oct. 22, 2018.
Roudebush, P, et al., "Evidence-Based Veterinary Dentistry; A Systematic Review of Homecare for Prevention of Periodontal Disease in Dogs and Cats", J Vet Dent 21 (1), 6-15 (2005).

*Primary Examiner* — J. E. Angell
(74) *Attorney, Agent, or Firm* — Viksnins Harris Padys Malen LLP

(57) ABSTRACT

The present invention relates to an isolated antisense oligonucleotide for use in a method of preventing or treating an inflammatory disease or condition of the buccal cavity in a canine subject, wherein said antisense oligonucleotide is directed against canine ICAM-1. The present invention further relates to compositions or articles of manufacture comprising said antisense oligonucleotide.

6 Claims, 5 Drawing Sheets

Figure 2:
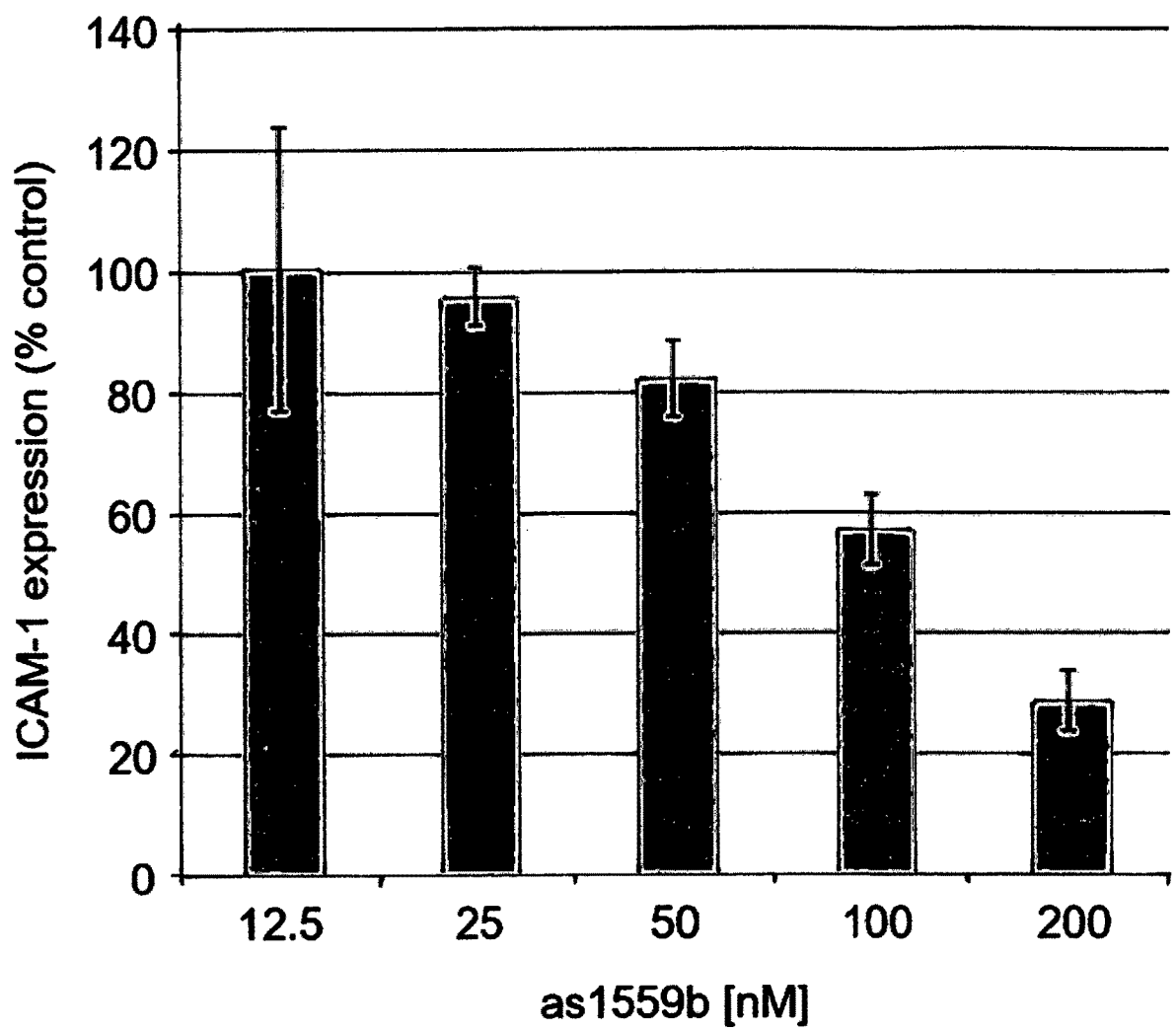

Specification includes a Sequence Listing.

NM_001003291

```
        1500       1510       1520       1530       1540       1550
         |          |          |          |          |          |
5'-TGTAGCCGCTTACCTCTATAACCGCCAGCGGAAGATCCAGAAATACAAGCT-3' si1559a            5'-CUCUAUAACCGCCAGCGGAtt-3'
                   3'-ttGAGAUAUUGGCGGUCGCCU-5' as1559a                          3'-GAGATATTGGCGGTCGCC-5'
as1559b                          3'-TATTGGCGGTCGCCTTCT-5'
as1559c                          3'ATTGGCGGTCGCCTTCTA-5'
``` negative controls sc1284(PTO): 5'-CAGGTGGTCAGATGGACC

Figure 1

ANTISENSE DRUGS AGAINST CANINE ICAM-1 FOR USE IN THE TREATMENT OF INFLAMMATION OF THE BUCCAL CAVITY

CROSS-REFERENCE TO RELATED APPLICATION(S)

This application claims the benefit of priority of EP Application No. 17001305.6, filed Jul. 28, 2017.

The present invention relates to an isolated antisense oligonucleotide for use in a method of preventing or treating an inflammatory disease or condition of the buccal cavity in a canine subject, wherein said antisense oligonucleotide is directed against canine ICAM-1. The present invention further relates to compositions or articles of manufacture comprising said antisense oligonucleotide.

Periodontitis, i.e., inflammation of the gingiva, the periodontal ligaments and the dental alveoli, and, in later stages, damage of the cementum and the jawbone, is the most prevalent disease of the buccal cavity on dogs. Even at a young age of five years, four out of five dogs display detectable periodontitis. This disease is not merely a cosmetic problem, but leads to deterioration of the general condition and can promote inflammation of internal organs.

In contradiction to the high prevalence of periodontitis in dogs, the disease is often diagnosed only late or even too late, since many of the related symptoms display a chronic and rather subtle progress. However, reestablishment of a healthy buccal cavity gets more and more difficult with disease progression.

Therefore, sustained dental hygiene is essential and regular controls and treatment at a veterinarian or a veterinary dentist are very important. Further, the owner of the dog can take several measures to prevent periodontitis, most importantly regularly brushing the dog's teeth. Moreover, chewing toys ensuring sufficient wear of the dog's teeth are available. Nevertheless, the need for simple and efficient means for the prevention and treatment of canine periodontitis is still great.

In this context, conventional treatment of canine periodontitis is based on empirics and rational designs, but does not consider the molecular patho-mechanisms of inflammation. Thus, it seems to be reasonable to assume that patho-mechanism-based treatment options bear superior chances for high efficacy.

Suppression of Intercellular Adhesion Molecule 1 (ICAM-1; CD54) for the prevention or treatment of inflammatory processes has been known in the art for some time. In humans, the use of antisense oligonucleotides directed against ICAM-1 has been described. However, means for the prevention or treatment of canine periodontitis based on the suppression of canine ICAM-1 have so far been elusive.

However, conventional treatment is empirical or partly rational but not related to molecular patho-mechanisms of inflammation. Thus, molecular mechanism-based treatments bear superior chances for high efficacy.

Accordingly, the technical problem underlying the present invention is to provide simple and efficient means for the prevention or treatment of canine periodontitis and other inflammatory diseases or conditions of the buccal cavity in canine subjects.

The solution to the above technical problem is achieved by the embodiments characterized in the claims.

In particular, in a first aspect, the present invention relates to an isolated antisense oligonucleotide for use in a method of preventing or treating an inflammatory disease or condition of the buccal cavity in a canine subject, said oligonucleotide comprising:

(i) the nucleotide sequence according to SEQ ID NO: 1; or (ii) a fragment of the nucleotide sequence according to SEQ ID NO: 1 having at least 14 nucleotides.

In this context, the specific antisense oligonucleotides used herein have been known in the art to suppress stimulated ICAM-1 expression in humans. However, the level of basal ICAM-1 expression in humans, as opposed to stimulated expression, is not suppressed by said oligonucleotides. In contrast, the present invention has identified that in canine subjects, basal ICAM-1 expression is advantageously and unexpectedly suppressed by the specific antisense oligonucleotides of the present invention to a significant extent.

In preferred embodiments, the inflammatory disease or condition of the buccal cavity to be prevented or treated according to the present invention is a periodontal disease or condition, more preferably a periodontal disease or condition selected from the group consisting of gingivitis, chronic periodontitis, aggressive periodontitis, periodontitis as a manifestation of systemic disease, necrotizing ulcerative gingivitis, necrotizing ulcerative periodontitis, abscesses of the periodontium, and combined periodontic-endodontic lesions.

In specific embodiments, the isolated antisense oligonucleotides of the present invention comprise a fragment of the nucleotide sequence according to SEQ ID NO: 1 having at least 14, at least 15, at least 16, or 17 nucleotides of SEQ ID NO: 1, i.e., said fragments have 14, 15, 16, or 17 nucleotides of SEQ ID NO: 1. Preferably, said oligonucleotides consists of said fragments, i.e., said oligonucleotides have a length of 14, 15, 16, or 17 nucleotides. Antisense oligonucleotides comprising said fragments preferably have a length of at least 14, 15, 16, or 17 nucleotides, and at most 50 bases or less, more preferably 40 bases or less, more preferably 30 bases or less, more preferably 25 bases or less, and most preferably 21 bases or less.

In a particularly preferred embodiment, the isolated antisense oligonucleotides of the present invention comprise the entire nucleotide sequence according to SEQ ID NO: 1. Preferably, said oligonucleotides consists of said nucleotide sequence, i.e., said oligonucleotides have a length of 18 nucleotides. Antisense oligonucleotides comprising said nucleotide sequence preferably have a length of 18 to 50 bases, more preferably 18 to 40 bases, more preferably 18 to 30 bases, more preferably 18 to 25 bases, and most preferably 18 to 21 bases.

The isolated antisense oligonucleotides of the present invention may comprise oligonucleotide modifications known in the art, e.g. modifications that increase the stability of the antisense oligonucleotide-target RNA complex such as LNA (locked nucleic acid) modifications.

In a second aspect, the present invention relates to a composition or article of manufacture comprising the isolated antisense oligonucleotide as defined above for the first aspect of the present invention.

Preferably, the composition or article of manufacture is a dog feed, a dog chewing gum, a dog chewing toy, a dog chewing bone, a dog dental chew, a dog tooth brush, a dog finger brush, a dog oral hygiene paste or gel, a dog mouthwash or dental rinse, a dog dental powder, a dog oral hygiene spray, a dog tooth polish, a dog toothpaste, or any formulation or mixture that improves oral hygiene and/or oral health. Means for incorporating the oligonucleotides of the present invention into respective compositions or articles of manufacture are not particularly limited and are known in the art.

The figures show:

FIG. 1:

Canine ICAM-1: local target sequence of antisense oligonucleotides and sequence positions according to NM_001003291 (antisense species as1559a (SEQ ID NO: 2), as1559b (SEQ ID NO: 1), as1559c (SEQ ID NO: 3), and the negative control, i.e., the scrambled sequence sc1284 (SEQ ID NO: 4)).

FIG. 2:

Dose-dependency of as1559b-mediated inhibition of basal gene expression of canine ICAM-1.

FIG. 3:

Suppression of basal expression of ICAM-1 by as1559-derived antisense species. Data measured at a cell density of 250,000 cells/well at seeding and the incubation time of 20 hrs are depicted in the left panel, measurements at a cell density of 500,000 cells/well at seeding and the incubation time of 44 hrs are depicted in the right panel. Here, DH82 cells were seeded in 12-well tissue culture plates at a density of 250,000 or 500,000 cells/well 20 hours prior to oligonucleotide treatment. Cells were transfected with 100 nM antisense oligonucleotides using Lipofectamine 2000 at a final concentration of 5 µg/mL for 4 hours, and harvested 20 hrs or 44 hrs after transfection for subsequent analyses as described herein. For further experimental details see section "Material and Methods" below. The error bars represent standard deviation from four PCR experiments performed in duplicate in cell culture.

FIG. 4:

Basal levels of canine gene expression of ICAM-1 can be inhibited by as1559b but not by as1559a nor as1559c (right group of bars) and it cannot be significantly be suppressed in human ECV-304 cells (left group of bars).

FIG. 5:

The antisense oligonucleotide as1559b is characterized by high reproducibility and effectiveness in canine cells. DH82 cells were seeded in 12-well tissue culture plates at a density of 250,000 cells/well 24 hours prior to oligonucleotide treatment. Cells were transfected with 100 nM antisense oligonucleotides using Lipofectamine 2000 at a final concentration of 5 µg/mL for 4 hours, and harvested 20 hrs after transfection for measuring mRNA levels of ICAM-1 by RTqPCR. For further experimental details see section "Materials and Methods" hereinafter. The error bars represent standard deviation of three independent biological experiments each performed in triplicate in cell culture.

The present invention will be further illustrated in the following examples without being limited thereto.

EXAMPLES

Material and Methods:

Cell Line and Cell Culture:

The cell line DH82 (Sigma-Aldrich Chemie GmbH, Munich, Germany) was derived from a ten year old male golden retriever with malignant histiocytosis. Cells were maintained in Dulbecco's MEM supplemented with 3.7 g/L $NaHCO_3$, 4.5 g/L D-glucose, stable glutamine, Na-pyruvate (Biochrom GmbH, Berlin, Germany), and 15% fetal calf serum (Biochrom GmbH, Berlin, Germany) at 37° C. in humidified atmosphere with 5% $CO_2$ and split 2 to 3 times a week.

The cell line ECV-304 is a derivative of the human urinary bladder carcinoma cell line T-24 which expresses ICAM-1 in an inducible manner. Cells were maintained in medium 199 containing HEPES (25 mM), 0.68 mM L-glutamine (Sigma-Aldrich, Deisenhofen, Germany) and 10% fetal calf serum (Invitrogen by Thermo Fisher Scientific, Carlsbad, USA) at 37° C. in humidified atmosphere with 5% CO2 and split 2 to 3 times a week. For stimulation of ICAM-1 (CD54) 200 U/ml interleukin 1ß (IL-1beta; PromoCell, Heidelberg, Germany) was added to the medium and cells were incubated overnight for 16 to 18 hours.

Transfection of Cells with asON:

DH82 cells were seeded in 12-well tissue culture plates at a density of $2.5 \times 10^5$ cells/well 20 hours prior to transfection with oligonucleotides. Preparation of the transfection mix with Lipofectamine 2000 (Invitrogen by Thermo Fisher Scientific, Carlsbad, USA) was carried out according to the manufacturer's instructions. Transfection of cells was performed with 0.5 mL Opti-MEM I medium (Invitrogen by Thermo Fisher Scientific, Carlsbad, USA) containing varying concentrations of asON (12.5 nM to 200 nM) and 5 µg/mL of Lipofectamine 2000 per well. Cells were incubated for 4 hours at 37° C., 5% $CO_2$. Subsequently, the transfection medium was replaced by fresh DMEM medium containing 15% FCS and incubated at 37° C., 5% $CO_2$ for 20 hours.

ECV-304 cells were seeded in 12-well culture plates at a density of $2.0 \times 10^5$ cells/well 15 hours prior to oligonucleotide treatment. Preparation of the transfection mix with Lipofectin (Invitrogen by Thermo Fisher Scientific, Carlsbad, USA) was carried out according to the manufacturer's instructions. The transfection of asON was performed with 1.0 mL Opti-MEM I medium (Invitrogen by Thermo Fisher Scientific, Carlsbad, USA) containing 100 nM of asON and 5 µg/mL of Lipofectin per well. The cells were incubated for 4 hours at 37° C., 5% CO2. Subsequently, the transfection medium was replaced by medium 199 containing 10% FCS. After an incubation of 4 hours at 37° C., 5% CO2 the medium was substituted with medium 199 containing 10% FCS and 200 U/mL IL-1beta to stimulate ICAM-1 expression for 16 to 18 hours. All cell culture experiments were performed in triplicate and at least in two independent runs.

RNA Extraction, cDNA Synthesis and Quantitative PCR:

Total cellular RNA was extracted from transfected cells using Qiazol reagent (Qiagen, Hilden, Germany). Subsequently, RNA was treated with TURBO DNase (Ambion by Thermo Fisher Scientific, Carlsbad, USA), according to the manufacturer's instructions. The yield and purity of RNA were determined by spectrophotometry.

Synthesis of cDNA was carried out by reverse transcription in a volume of 20 µl with equal amounts of RNA (3 µg) using the RevertAid First Strand cDNA Synthesis Kit and 200 ng random hexamer primer (Thermo Fisher Scientific, Carlsbad, USA).

Quantitative PCR was performed using the ABI Prism 7900HT Sequence Detection System (Applied Biosystems, Darmstadt, Germany) and SYBR Select Master Mix (Thermo Fischer, Carlsbad, USA). Canine ICAM-1 cDNA (3 ng/PCR) was amplified with the forward primer 5'-TGACAACCATTGTCATCTTAGGAA-3' (SEQ ID NO: 5) and reverse primer 5'-GGTGTGTTCAGCTTCATGGC-3' (SEQ ID NO: 6) resulting in a fragment of 124 bp. Canine 18S cDNA (0.03 ng/PCR) was amplified with forward primer, 5'-CACATCCAAGGAAGGCAGCAG-3' (SEQ ID NO: 7) and reverse primer, 5'-GACTTGCCCTCCAATGGATCC-3' (SEQ ID NO: 8) resulting in a product of 152 bp. All qPCR runs were conducted at 95° C. for 2 minutes, and then 40 cycles of 95° C. for 15 seconds and 60° C. for 60 seconds. The specificity of the reaction was verified by melt curve analysis. Each reaction was run in triplicate. The mRNA expression level of each sample was normalized to the amount of 18S rRNA and analyzed by the comparative ΔCt method and expressed as relative amounts to negative control (sc1284).

For experiments with human ECV-304 cells, total RNA was extracted from transfected cells using RNeasy mini kit including treatment with RNase-free DNase I (Qiagen, Hilden, Germany). The yield and purity of RNA were determined by spectrophotometry. Synthesis of cDNA was carried out using random hexamer primers and Superscript II RNase H-reverse transcriptase according to the manufacturer's specifications (Invitrogen by Thermo Fisher Scientific, Carlsbad, USA). Gene expression of ICAM-1 was analyzed by quantitative PCR. Therefore, 100 ng of reverse transcribed RNA was analyzed using SYBR green PCR core reagents (Eurogentec, Seraing, Belgium). The reaction was carried out in 50 μl containing 300 nM gene-specific 5' and 3' primers, respectively, and assayed with the GeneAmp 5700 sequence detection system (Applied Biosystems, Darmstadt, Germany). Human ICAM-1 cDNA was amplified with the forward primer 5'-GCCACTTCTTCTGTAAGTCTGTGGG-3' (SEQ ID NO: 9) and reverse primer 5'-CTACCGGCCCTGGGACG-3' (SEQ ID NO: 10). Samples were normalized using primers specific to cDNA encoding human GAPDH (forward primer, 5'-AACAGCGACACCCACTCCTC-3' (SEQ ID NO: 11) and reverse primer, 5'-GGAGGGGAGATTCAGTGTGGT-3' (SEQ ID NO: 12)). Within each PCR-run all amplification reactions were performed in triplicate. Results are expressed as percentage of expression with control ON which was set 100%.

Example 1

Canine ICAM-1 Expression is Suppressed by as1559b in a Concentration-Dependent Way.

FIG. 2 shows that the basal level of ICAM-1 expression in canine DH82 cells (100%) can be suppressed by the antisense oligonucleotide as1559b in a concentration-dependent manner. This experiment was performed as described above. In detail, 20 hours after transfection, RNA was isolated and levels of ICAM-1 mRNA as well as 18S rRNA were measured in triplicate by RT-qPCR. The ICAM-1 expression level of each sample was first normalized to the amount of 18S rRNA and then compared to cells transfected with the control oligonucleotide (sc1284) at the same total dose. FIG. 2 shows the mean and the standard deviation of the RT-qPCR-based quantification in triplicate.

In this context, it should be noted that this concentration-dependent suppression of ICAM-1 occurs at the level of basal gene expression, rather than on the cytokine-stimulated level which was never observed in the human system. In human cells, basal gene expression could not be affected by asON under comparable experimental conditions.

Example 2

Substantial Suppression of Basal Gene Expression of ICAM-1 by as1559b.

Figure 3:
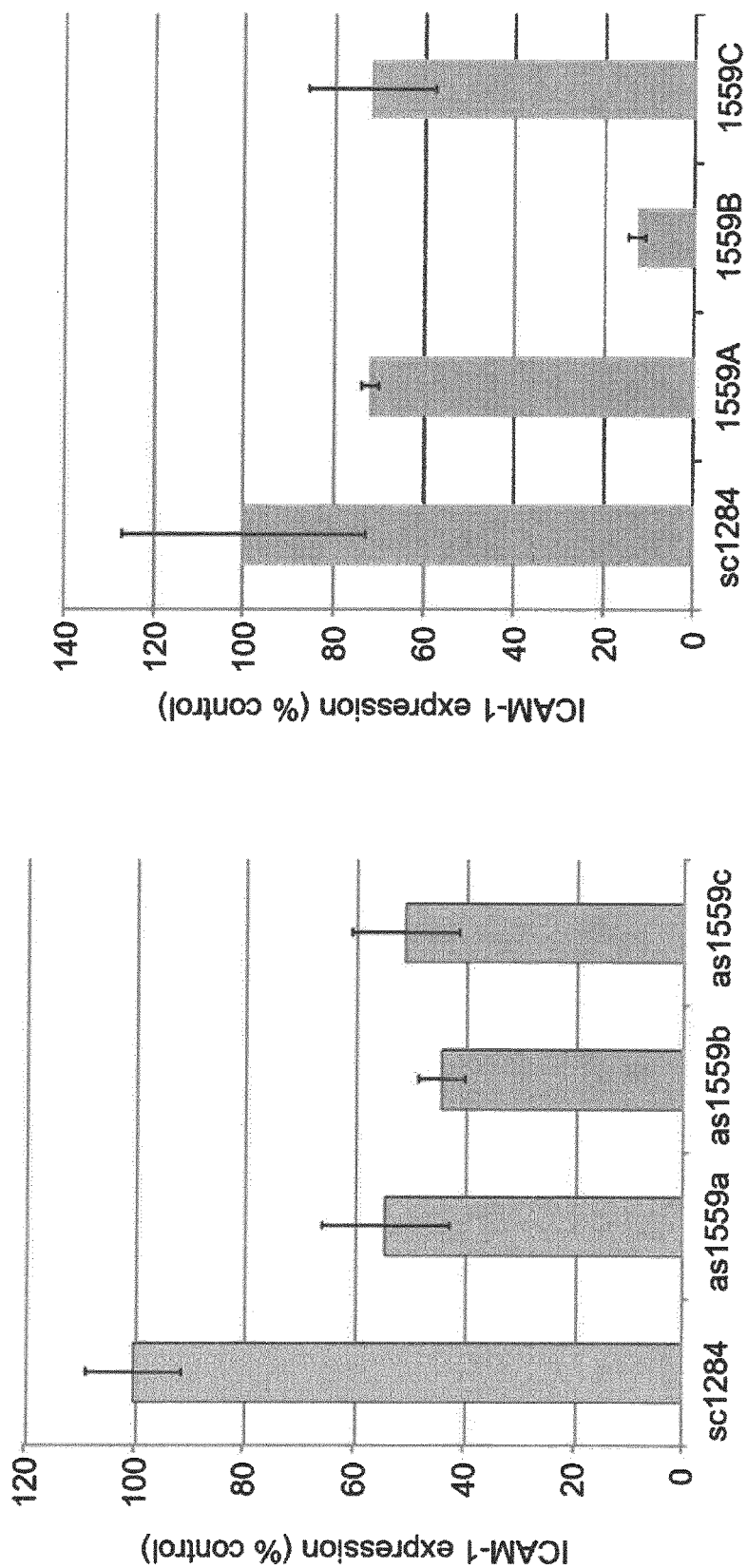
Figure 5:
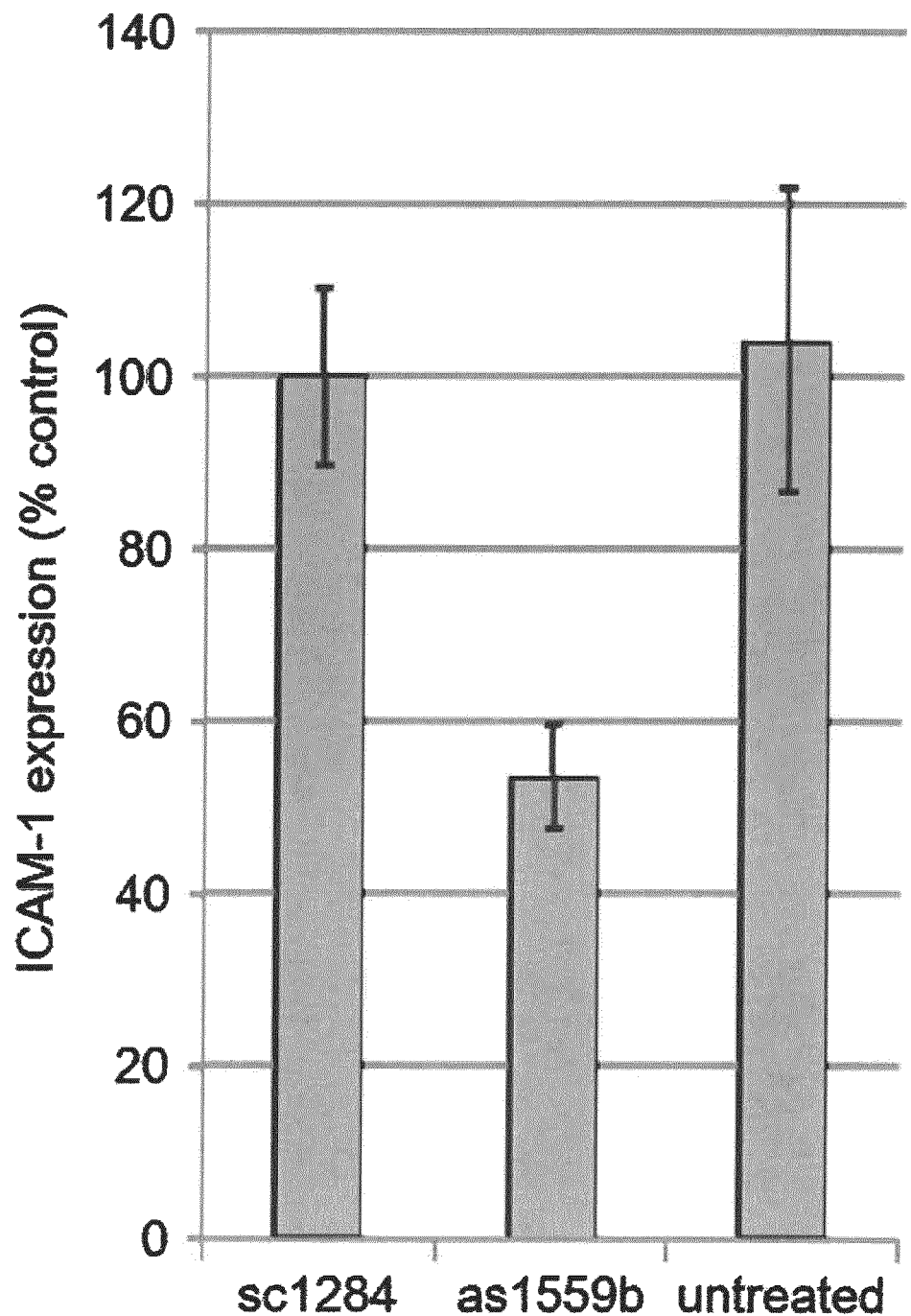

All three as1559-related antisense oligonucleotides suppress the basal level of gene expression of ICAM-1 in canine DH82 cells. However, the greatest extent of target inhibition is observed in the use of as1559b (FIGS. 3, 5). In this experiment, DH82 cells (250.000 cells/well) were transfected with the oligonucleotides as1559a, as1559b, or as1559c, respectively at 100 nM final concentration in Opti-MEM I medium containing 5 μg/ml Lipofectamine 2000 for 4 hours. Cells were harvested 20 hours after transfection. RNA isolation, cDNA synthesis and quantitative PCR were performed as described above. The ICAM-1 expression level of each sample was first normalized to the amount of 18S rRNA and then compared to cells transfected with the control oligonucleotide (sc1284) at the same total dose. FIGS. 2, 3 and 5 show the mean and the standard deviation of the RT-qPCR-based quantification in triplicate.

While increased efficacy of 1559b versus as1559a and as1559c is significant though moderate at lower initial cell density and shorter observation time, as1559b performs substantially more efficient at higher initial cell density and longer observation time. In summary, it is concluded that as1559b shows a surprisingly strong inhibition of basal levels of ICAM-1 expression which is robust and reproducible in the range of 50% of normal expression levels, depending on cell-density and duration of exposure to as1559b.

Example 3

The antisense oligonucleotide as1559b is surprisingly efficient in canine cells.

All three antisense species against ICAM-1, i.e., as1559a, as1559b, and 1559c, respectively, are directed against the same local target motif of their target, i.e., ICAM-1 mRNA (FIG. 1).

Figure 4:
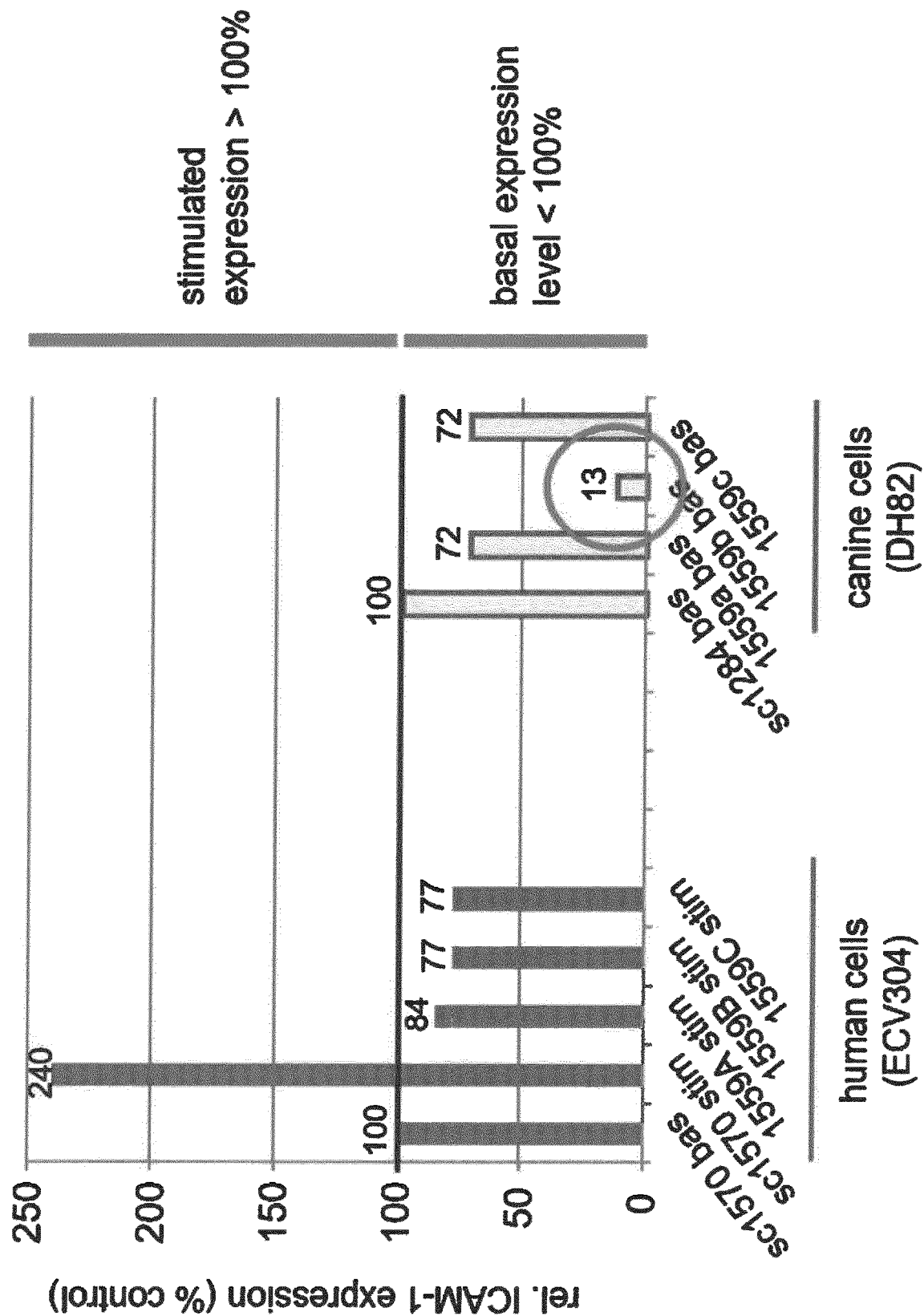

Regarding the gene expression of ICAM-1, it should be noted that this is sub-divided into the basal level and the stimulated range (cf. FIG. 4, right panel and Y-axis). This division is important because of the different responsiveness to oligonucleotide-based inhibitors. While it is quite easy to completely suppress the stimulated range of ICAM-1 gene expression in human cells, and presumably in other mammals, it is very challenging to down-regulate the basal expression level which is set 100% in this figure. Most antisense oligonucleotides and also many siRNAs do not significantly affect ICAM-1 expression in this basal range.

The data shown in FIG. 4 demonstrate that none of the three antisense oligonucleotides shows substantial effects on basal gene expression in human cells (left panel). This is reflected by the lack of strong effects mediated by as1559a and as1559c in canine cells (right panel). For two reasons it is surprising that as1559b down-regulates ICAM-1 to the level of 13% in canine cells (right panel, circle). Firstly, the extent of inhibition by as1559b has not been observed in the use of antisense oligonucleotides so far. Secondly, as1559b is highly active in the canine system which one would not have predicted from the human system.

The present invention relates to the following nucleotide sequences.

Antisense oligonucleotide as1559b

SEQ ID NO: 1

TCTTCCGCTGGCGGTTAT

Antisense oligonucleotide as1559a

SEQ ID NO: 2

CCGCTGGCGGTTATAGAG

Antisense oligonucleotide as1559c

SEQ ID NO: 3

ATCTTCCGCTGGCGGTTA

Scrambled negative control oligonucleotide sc1284

SEQ ID NO: 4

CAGGTGGTCAGATGGACC

| Primer sequence | SEQ ID NO: 5 |
|---|---|
| TGACAACCATTGTCATCTTAGG | |
| Primer sequence | SEQ ID NO: 6 |
| GGTGTGTTCAGCTTCATGGC | |
| Primer sequence | SEQ ID NO: 7 |
| CACATCCAAGGAGGCAGCAG | |
| Primer sequence | SEQ ID NO: 8 |
| GACTTGCCCTCCAATGGATCC | |
| Primer sequence | SEQ ID NO: 9 |
| GCCACTTCTTCTGTAAGTCTGTGGG | |
| Primer sequence | SEQ ID NO: 10 |
| CTACCGGCCCTGGGACG | |
| Primer sequence | SEQ ID NO: 11 |
| AACAGCGACACCCACTCCTC | |
| Primer sequence | SEQ ID NO: 12 |
| GGAGGGGAGATTCAGTGTGGT | |
| Partial sequence of *Canis lupus familiaris* ICAM-1 mRNA | SEQ ID NO: 13 |
| TGTAGCCGCTTACCTCTATAACCGCCAGCGGAAGATCCAGAAATACAAGCT | |
| Strand of si1559a | SEQ ID NO: 14 |
| CUCUAUAACCGCCAGCGGAUU | |
| Strand of si1559a | SEQ ID NO: 15 |
| UCCGCUGGCGGUUAUAGAGUU | |

The invention claimed is:

1. A method of treating an inflammatory disease or condition of the buccal cavity in a canine subject, the method comprising administering an isolated antisense oligonucleotide to the canine subject to thereby treat the inflammatory disease or condition, wherein said oligonucleotide consists of the nucleotide sequence according to SEQ ID NO: 1.

2. The method according to claim 1, wherein the inflammatory disease or condition of the buccal cavity is a periodontal disease or condition.

3. The method according to claim 2, wherein the periodontal disease or condition is selected from the group consisting of gingivitis, chronic periodontitis, aggressive periodontitis, periodontitis as a manifestation of systemic disease, necrotizing ulcerative gingivitis, necrotizing ulcerative periodontitis, abscesses of the periodontium, and combined periodontic-endodontic lesions.

4. The method according to claim 1, wherein the oligonucleotide suppresses basal ICAM-1 expression.

5. The method according to claim 1, wherein the administration of the isolated antisense oligonucleotide to the canine subject is performed using a composition or an article of manufacture comprising said oligonucleotide.

6. The method according to claim 5, wherein the composition or article of manufacture is a dog feed, a dog chewing gum, a dog chewing toy, a dog chewing bone, a dog dental chew, a dog tooth brush, a dog finger brush, a dog oral hygiene paste or gel, a dog mouthwash or dental rinse, a dog dental powder, a dog oral hygiene spray, a dog tooth polish, or a dog toothpaste.

* * * * *

```
                        SEQUENCE LISTING

<160> NUMBER OF SEQ IDS: 15

<210> SEQ ID NO 1
<211> LENGTH: 18
<212> TYPE: DNA
<213> ORGANISM: Artificial sequence
<220> FEATURE:
<223> OTHER INFORMATION: Antisense oligonucleotide

<400> SEQUENCE: 1
tcttccgctg gcggttat                                                   18

<210> SEQ ID NO 2
<211> LENGTH: 18
<212> TYPE: DNA
<213> ORGANISM: Artificial sequence
<220> FEATURE:
<223> OTHER INFORMATION: Antisense oligonucleotide

<400> SEQUENCE: 2
ccgctggcgg ttatagag                                                   18

<210> SEQ ID NO 3
<211> LENGTH: 18
<212> TYPE: DNA
<213> ORGANISM: Artificial sequence
<220> FEATURE:
<223> OTHER INFORMATION: Antisense oligonucleotide

<400> SEQUENCE: 3
atcttccgct ggcggtta                                                   18

<210> SEQ ID NO 4
<211> LENGTH: 18
<212> TYPE: DNA
<213> ORGANISM: Artificial sequence
<220> FEATURE:
<223> OTHER INFORMATION: Scrambled negative control oligonucleotide

<400> SEQUENCE: 4
caggtggtca gatggacc                                                   18
```

```
<210> SEQ ID NO 5
<211> LENGTH: 24
<212> TYPE: DNA
<213> ORGANISM: Artificial sequence
<220> FEATURE:
<223> OTHER INFORMATION: Primer sequence

<400> SEQUENCE: 5
tgacaaccat tgtcatctta ggaa                                              24

<210> SEQ ID NO 6
<211> LENGTH: 20
<212> TYPE: DNA
<213> ORGANISM: Artificial sequence
<220> FEATURE:
<223> OTHER INFORMATION: Primer sequence

<400> SEQUENCE: 6
ggtgtgttca gcttcatggc                                                   20

<210> SEQ ID NO 7
<211> LENGTH: 21
<212> TYPE: DNA
<213> ORGANISM: Artificial sequence
<220> FEATURE:
<223> OTHER INFORMATION: Primer sequence

<400> SEQUENCE: 7
cacatccaag gaaggcagca g                                                 21

<210> SEQ ID NO 8
<211> LENGTH: 21
<212> TYPE: DNA
<213> ORGANISM: Artificial sequence
<220> FEATURE:
<223> OTHER INFORMATION: Primer sequence

<400> SEQUENCE: 8
gacttgccct ccaatggatc c                                                 21

<210> SEQ ID NO 9
<211> LENGTH: 25
<212> TYPE: DNA
<213> ORGANISM: Artificial sequence
<220> FEATURE:
<223> OTHER INFORMATION: Primer sequence

<400> SEQUENCE: 9
gccacttctt ctgtaagtct gtggg                                             25

<210> SEQ ID NO 10
<211> LENGTH: 17
<212> TYPE: DNA
<213> ORGANISM: Artificial sequence
<220> FEATURE:
<223> OTHER INFORMATION: Primer sequence

<400> SEQUENCE: 10
ctaccggccc tgggacg                                                      17

<210> SEQ ID NO 11
<211> LENGTH: 20
<212> TYPE: DNA
<213> ORGANISM: Artificial sequence
<220> FEATURE:
<223> OTHER INFORMATION: Primer sequence
```

```
<400> SEQUENCE: 11
aacagcgaca cccactcctc                                                     20

<210> SEQ ID NO 12
<211> LENGTH: 21
<212> TYPE: DNA
<213> ORGANISM: Artificial sequence
<220> FEATURE:
<223> OTHER INFORMATION: Primer sequence

<400> SEQUENCE: 12
ggaggggaga ttcagtgtgg t                                                   21

<210> SEQ ID NO 13
<211> LENGTH: 51
<212> TYPE: DNA
<213> ORGANISM: Canis lupus familiaris

<400> SEQUENCE: 13
tgtagccgct tacctctata accgccagcg gaagatccag aaatacaagc t                  51

<210> SEQ ID NO 14
<211> LENGTH: 21
<212> TYPE: DNA
<213> ORGANISM: Artificial sequence
<220> FEATURE:
<223> OTHER INFORMATION: strand of si1559a

<400> SEQUENCE: 14
cucuauaacc gccagcggat t                                                   21

<210> SEQ ID NO 15
<211> LENGTH: 21
<212> TYPE: DNA
<213> ORGANISM: Artificial sequence
<220> FEATURE:
<223> OTHER INFORMATION: strand of si1559a

<400> SEQUENCE: 15
uccgcuggcg guuauagagt t                                                   21
```